United States Patent [19]

Hornig

[11] Patent Number: 5,073,113
[45] Date of Patent: Dec. 17, 1991

[54] METHOD OF MANUFACTURING METALLIC TOOTH PARTS

[75] Inventor: Wolfgang Hornig, Sandhausen, Fed. Rep. of Germany

[73] Assignee: Prodenta AG, Switzerland

[21] Appl. No.: 626,686

[22] Filed: Dec. 12, 1990

[51] Int. Cl.$^5$ ............................................... A61C 5/10
[52] U.S. Cl. ................................................... 433/223
[58] Field of Search ............. 433/223, 74, 167, 200.1, 433/206, 208, 213, 214, 215, 218; 269/16, 17, 18, 19

[56] References Cited

U.S. PATENT DOCUMENTS

| | | | |
|---|---|---|---|
| 397,320 | 2/1889 | Ward | 433/200.1 |
| 1,612,605 | 12/1926 | Buenaventura | 433/200.1 |
| 3,552,018 | 1/1971 | Zahn | 433/74 |
| 3,636,632 | 1/1972 | Costa et al. | 433/213 |
| 4,363,627 | 12/1982 | Windeler | 433/213 |
| 4,562,882 | 1/1986 | Alleluia | 164/529 |
| 4,776,795 | 10/1988 | Hornig | 433/223 |
| 4,820,387 | 4/1989 | Yamashita et al. | 204/4 |

FOREIGN PATENT DOCUMENTS

| | | | |
|---|---|---|---|
| 1919652 | 11/1970 | Fed. Rep. of Germany | 433/200.1 |
| 3320902 | 3/1985 | Fed. Rep. of Germany | 433/206 |
| 400089 | 10/1933 | United Kingdom | 433/201.1 |

Primary Examiner—John J. Wilson
Attorney, Agent, or Firm—Davis, Bujold & Streck

[57] ABSTRACT

In the process for producing metal partial denture prostheses according to the invention, a mold is made from the jaw or tooth to be treated by means of an electrically non-conducting material, then the inner wall of that mold is provided with an electrically conducting layer. Thereafter the inner space of the mold and of the electrically conducting layer is filled with a filler material into which is introduced at least one rod after which the positive pattern produced by the electrically conducting layer and the filler material then separated from the mold. The filler material is an electrically non-conducting plastic whose volume enlarges when heated. The positive pattern is introduced in a heated electrolyte in which one or more layers of high-melting point metals or noble metals are galvanically deposited on the electrically conducting layer on the positive pattern. The positive pattern with the galvanically deposited layer is then removed from the electrolyte and, after cooling to approximately room temperature, the galvanic layer of high-melting metal or noble metal that forms the partial denture prosthesis is separated from the positive pattern without damaging it.

5 Claims, 2 Drawing Sheets

METHOD OF MANUFACTURING METALLIC TOOTH PARTS

This invention relates to a process for producing metal partial denture prostheses such as crowns, parts of bridges and bases for prosthesis in which a mold is produced from the tooth or jaw to be treated using an electrically non-conducting material, then the inner wall of said mold is provided with an electrically conducting layer, thereafter the inner space of the mold and of the electrically conducting layer is lined with a filler material into which is introduced at least one rod, after which the positive pattern formed by the electrically conducting layer and the filler material is separated from the mold.

A process of the above kind has been disclosed in German Patent 36 07 915. In this process, in order to produce, easily and at reasonable cost, partial denture prostheses of high precision, without a complicated process to produce from a first pattern a second pattern upon which the partial denture prosthesis is then mounted, there is applied on the positive pattern an intermediate layer of a base metal after which one or several layers of high-melting point metals or noble metals are galvanically applied to said intermediate layer. After this the filler material, the innermost electrically conducting layer and the intermediate layer are removed and optionally porcelain and/or plastic is applied to the partial denture prosthesis thus resulting.

It has thus become possible to produce partial denture prostheses which have a great homogeneity of the metal and obtain a reduction of weight of from 70 to 80% compared to the prior art casting process. As a result of the elimination of the finishing operation, considerable expenses are saved, eliminating at the same time sources of error which in the casting process occur due to the expansion reaction of the metals upon heating and to the contraction reaction upon cooling.

An object of the present invention is to further simplify such process and thereby considerably to reduce the expenses that result in the production of metal partial denture prostheses.

According to the present invention, it is proposed to use as a filler material an electrically non-conducting material whose volume increases under the action of heat, to introduce the positive pattern into a heated electrolyte in which one or more layers of high-melting metals or noble metals are galvanically deposited over the electrically conducting layer on the positive pattern, then to remove the positive pattern with the galvanically deposited layer upon the electrolyte and after cooling to substantially room temperature to separate the galvanic layer of high-melting metal or noble metal that forms the partial denture prosthesis from the positive pattern without damaging it.

The rod advantageously consists of an electrically conducting material which is introduced in the filler material until the tip touches the electrically conducting layer on the inner wall of the mold.

In a preferred embodiment, prior to introduction in the electrolyte, the end of the rod projecting from the underside of the positive pattern is connected by means of a shrinkdown tube with the end of a conducting cable. A tube of teflon or other bath-compatible material can be used as shrinkdown tube.

A conducting lacquer can be sprayed on the inner wall of the mold as the conducting layer, while a polystyrene is advantageously adequate as the filler material and preferably the noble metal is gold galvanically deposited.

The finished partial denture prosthesis is especially easily separated from the positive pattern by feeding compressed air.

The process of the invention can be carried out especially easily and quickly. After introducing the positive pattern in the electrolyte heated to about 60° to about 80° C., the plastic, such as polystyrene, that forms the filler material expands together with the electrically conducting lacquer applied to its surface so that as result of this enlargement in volume there forms the cement gap later required for permanent fastening of the partial denture prosthesis. After cooling of the positive pattern, the metal partial denture prosthesis thus resulting can be specially easily detached therefrom by using compressed air without the positive pattern being in the least damaged.

In this process the partial prosthesis is also produced on the first pattern whereby error resulting from the use of a second or intermediate pattern are eliminated.

The invention is explained in more detail herebelow, by way of example, with reference to the accompanying drawings, in which.

Figure 1:
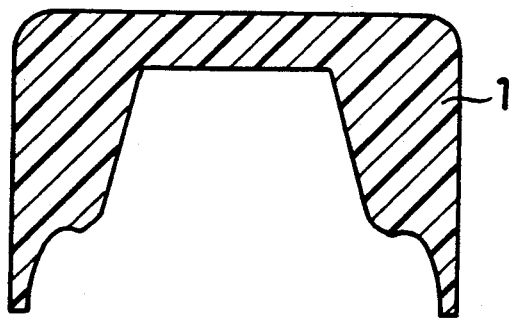
FIG. 1 is a cross-section through a tooth mold.

FIG. 1 diagrammatically shows a section through a mold of a tooth, the mold 1 consisting of an electrically non-conducting traditional material.

Figure 2:
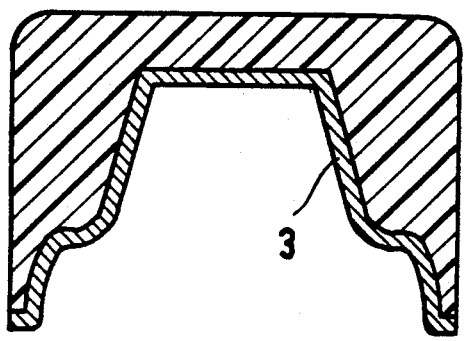
FIG. 2 is a cross-section of the mold of FIG. 1 with its cavity coated with a conducting lacquer.

FIG. 2 shows, the inner wall of the mold provided with an electrically conducting layer 3, consisting, for instance, of a sprayable conducting lacquer which has a certain elasticity.

Figure 3:
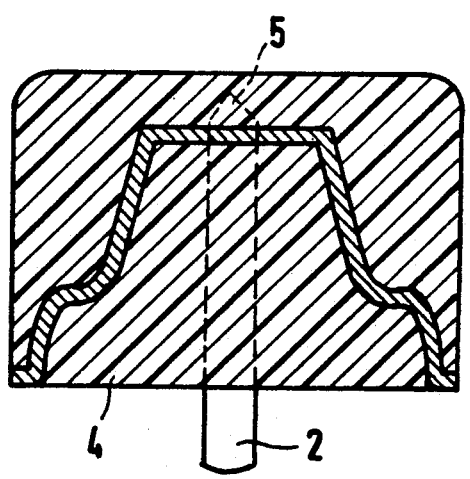
FIG. 3 is a cross-section of the coated mold of FIG. 2 filled with a filler.

FIG. 3 shows, on the inner space of the mold 1 and of the electrically conducting layer 3, a filler material 4 of an electrically non-conducting material. While said filler material is still soft, one or more rods 2 are pressed therein specifically until the tip 5 of the rod 2 has completely penetrated the filler material 4 and either touches or penetrates the electrically conducting layer 3.

Figure 4:
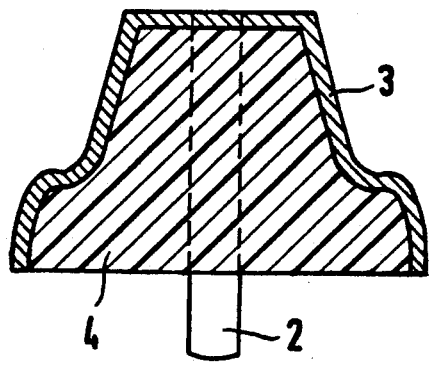
FIG. 4 is a cross-section of a positive pattern molded in the mold of FIG. 1.

FIG. 4 shows the positive pattern formed by the filler material 4 and the electrically conducting layer 3 after separation from the mold 1, the tip of the rod 4 that penetrates the electric layer 3 is removed according to FIG. 4, such as by cutting off or grinding.

Figure 5:
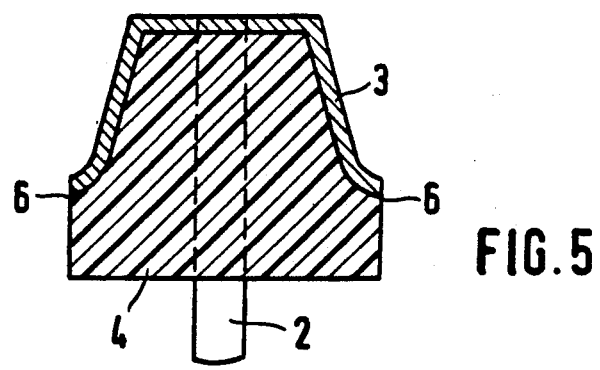
FIG. 5 is a cross-section of a trimmed positive pattern of FIG. 4.

FIG. 5 shows a bead 6 projecting through the flesh of the tooth and surrounding the base part of the positive pattern 3. The filler material 4 is now for the most part cut off so that the positive pattern substantially assumes the shape shown in FIG. 5.

Figure 6:
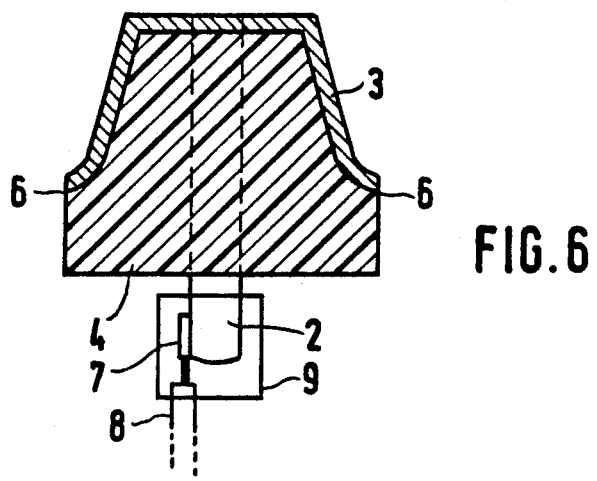
FIG. 6 is the pattern of FIG. 5 connected to a conductor.

FIG. 6 shows the preparation for receiving the galvanic coating of the positive pattern 3, 4 in which the rod 2 which consists of an electrically conducting material is connected with the stripped end 7 of an electric conductor 8 in a manner such that said end 7, and the end of the conducting rod 2 projecting from the filler material, is surrounded by a shrinkdown tube 9.

Figure 7:
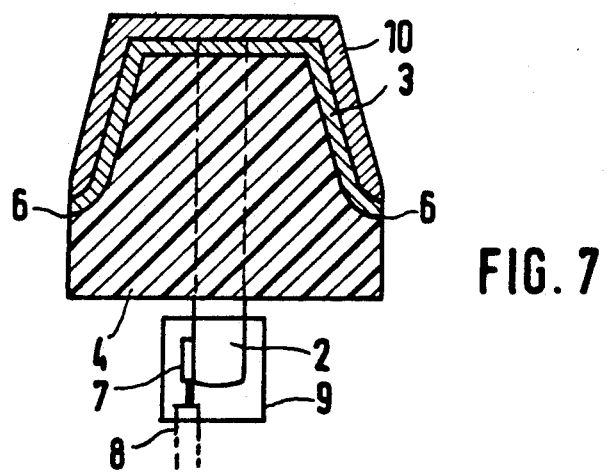
FIG. 7 is the pattern of FIG. 6 following deposition of a noble metal thereon.

The positive pattern 3, 4 thus prepared is now introduced into an electrolyte heated to about 60° to about 80° C. of a small galvanizing device and the free end of the cable 8 is connected with the negative pole of a source of current. By adequately selecting the material for the filler, for example, polystyrene, the latter, as result of the heating in the electrolyte, expands together with the electrically conducting layer 3 as function of the elevation in temperature after which following this desired expansion, the current is caused to flow through the galvanizing device to effect deposit of one or more layers 10 (FIG. 7) of high-melting point metals or noble metals, especially gold. After deposition of the layer(s) 10 of sufficient thickness (or also of consecutive layers of different metals, such as by immersion in different galvanizing devices), the positive pattern together with the deposited layer 10 is removed from the electrolyte and cooled to room temperature. As a result the filler material 4 contracts together with the electrically conducting layer 3 thereby permitting the finished partial denture prosthesis 10, such as a crown jacket, to be lifted off without great use of force (e.g. by means of a short blast of compressed air), and produces a cement gap needed for the subsequent fastening of the crown jacket 10 on the stump of the tooth by an adhesive which fills the gap produced. Hence, the crown jacket 10 is somewhat enlarged as result of the expansion of the positive pattern 3, 4.

Figure 8:
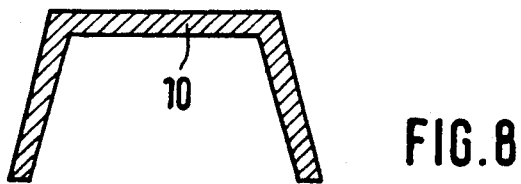
FIG. 8 is a cross-section of a finished dental prosthesis.

FIG. 8 shows the finished diagrammatic partial denture prosthesis 10 after being separated from the positive pattern. It is to be observed that absolutely no damage to the positive pattern 3, 4 results from the separation of the partial denture prosthesis 10, since it can be upwardly removed due to the limitation of the bead 6 without leaving traces of removal in the process.

The process according to the invention is adequate not only for producing crown jackets, as diagrammatically shown in the figures, but also for the production of other metal partial denture prostheses such as parts of bridges and bases for prostheses, it being in particular possible to produce the bridge supports in analogous manner to the crown jackets. The required intermediate member for the bridges is here adapted in the traditional manner.

I claim:

1. A process for producing metal denture prostheses wherein a mold defining a cavity representing the mouth part to be treated is made from an electrically non-conducting material, the inner cavity is then lined with an electrically conducting layer and the lined cavity is filled with a filler material into which at least one rod is introduced to form a positive pattern formed by the electrically conducting layer, the filler material and said rod, and the positive pattern is removed from the mold characterized by using as filler material an electrically non-conducting material suitable for emmersion in an electrolyte which increases in volume under the action of heat, introducing the positive pattern into a heated electrolyte and electrolytically depositing at least one layer of a metal on said electrically conducting layer of said positive pattern to form thereby the denture prosthesis, removing said positive pattern with the galvanically deposited layer from said electrolyte, and after cooling, separating the partial denture prosthesis from the positive pattern.

2. A process according to claim 1, characterized by introducing said rod of electrically conducting material into the filler material until its tip engages the electrically conducting layer on the inner wall of said mold.

3. A process according to claim 2, characterized by, prior to introducing the positive pattern into said electrolyte, an end of the rod that projecting from the underside of said positive pattern is connected with the end of an electrically conducting cable by means of shrinkdown tube.

4. A process according to claim 1, characterized by the electrically conducting layer being an electrically conducting lacquer, using polystyrene as the filler material and galvanically depositing gold as the metal.

5. A process according to claim 1, characterized by separating the finished partial denture prosthesis from said positive pattern by means of compressed air.

* * * * *